US009505820B2

(12) United States Patent
Azizova et al.

(10) Patent No.: US 9,505,820 B2
(45) Date of Patent: Nov. 29, 2016

(54) HAIR TREATMENT COMPOSITION WITH NATURALLY - DERIVED PEPTIDE IDENTICAL TO HUMAN HAIR

(75) Inventors: Marina Azizova, New Canaan, CT (US); Elizabeth A. Archibald, Putnam Valley, NY (US); Rushi Tasker, Trumbull, CT (US); Amrit Chaudhuri, Littleton, MA (US)

(73) Assignee: Zotos International, Inc., Darien, CT (US)

( * ) Notice: Subject to any disclaimer, the term of this patent is extended or adjusted under 35 U.S.C. 154(b) by 351 days.

(21) Appl. No.: 12/874,034

(22) Filed: Sep. 1, 2010

(65) Prior Publication Data

US 2012/0052034 A1    Mar. 1, 2012

(51) Int. Cl.
| | |
|---|---|
| A61K 8/65 | (2006.01) |
| C07K 7/06 | (2006.01) |
| A61Q 5/06 | (2006.01) |
| A61Q 5/02 | (2006.01) |
| A61Q 5/12 | (2006.01) |
| C07K 14/47 | (2006.01) |
| A61Q 5/00 | (2006.01) |

(52) U.S. Cl.
CPC .............. *C07K 14/4741* (2013.01); *A61K 8/65* (2013.01); *A61Q 5/00* (2013.01); *A61Q 5/065* (2013.01); *A61Q 5/12* (2013.01)

(58) Field of Classification Search
CPC .......... A61K 8/65; A61Q 5/00; A61Q 5/065; A61Q 5/12; B21D 35/006; C07K 14/4741
USPC ...................... 424/70.14, 70.6; 530/329, 330
See application file for complete search history.

(56) References Cited

U.S. PATENT DOCUMENTS

| | | | |
|---|---|---|---|
| 3,968,218 A | 7/1976 | Bouillon et al. | |
| 4,283,386 A | 8/1981 | Van Scott et al. | |
| 4,839,168 A | 6/1989 | Abe et al. ........................ | 424/74 |
| 4,975,274 A | 12/1990 | Iannucci et al. | |
| 5,389,362 A | 2/1995 | Mahieu et al. | |
| 5,626,855 A | 5/1997 | Philippe | |
| 5,711,942 A | 1/1998 | Eicken et al. | |
| 5,714,630 A | 2/1998 | Philippe | |
| 6,010,708 A | 1/2000 | Ogihara et al. | |
| 6,572,845 B2 | 6/2003 | Ensley | |
| 7,151,079 B2 | 12/2006 | Fack et al. | |
| 7,220,405 B2 | 5/2007 | Huang et al. | |
| 7,241,452 B2 | 7/2007 | Veeger et al. | |
| 7,300,469 B2 | 11/2007 | Fessmann et al. | |
| 7,300,647 B1 | 11/2007 | O'Toole et al. | |
| 7,736,633 B2 | 6/2010 | Beck et al. | |
| 7,759,460 B2 | 7/2010 | Huang et al. | |
| 2001/0006664 A1 | 7/2001 | Ensley ........................... | 424/401 |
| 2003/0228353 A1* | 12/2003 | Cowsar ........................ | 424/445 |
| 2005/0037430 A1 | 2/2005 | Khan et al. | |
| 2006/0165635 A1 | 7/2006 | Kelly et al. | |
| 2006/0171885 A1* | 8/2006 | Janssen et al. .............. | 424/1.69 |
| 2006/0272103 A1 | 12/2006 | Barbarat | |
| 2008/0026017 A1 | 1/2008 | Majeed et al. | |
| 2008/0069784 A1 | 3/2008 | Millikin et al. | |
| 2008/0107614 A1 | 5/2008 | Fahnestock et al. | |
| 2009/0149362 A1 | 6/2009 | Kalidindi | |
| 2010/0196302 A1 | 8/2010 | Vermelho et al. ........... | 424/70.1 |

FOREIGN PATENT DOCUMENTS

| | | |
|---|---|---|
| CA | 1178208 | 11/1984 |
| DE | 4344141 | 7/1995 |
| DE | 10361854 | 7/2005 |
| EP | 0542309 | 5/1993 |
| EP | 0780117 | 6/1997 |
| EP | 1557156 | 7/2005 |
| JP | 9029819 | 2/1997 |
| JP | 9124434 | 5/1997 |
| JP | 10017427 | 1/1998 |
| JP | 10059829 | 3/1998 |
| JP | 10130128 | 5/1998 |
| JP | 10337466 | 12/1998 |
| JP | 2002051770 | 2/2002 |
| WO | 9318736 | 9/1993 |
| WO | 9517157 | 6/1995 |
| WO | 0051545 | 9/2000 |
| WO | 0051555 | 9/2000 |
| WO | 0051556 | 9/2000 |
| WO | WO 2004003018 A1 * | 1/2004 ........... C07K 14/705 |
| WO | 2005079731 | 9/2005 |

OTHER PUBLICATIONS

UniProt Protein Database, Keratin, type I cuticular Ha5, Protein Accession Q92764, pp. 1-11, accessed on Sep. 10, 2014.*
UniProt Protein Database, Keratin, type II cuticular Hb5, Protein Accession P78386, pp. 1-11, accessed on Sep. 10, 2014.*
UniProt Protein Database, Keratin, type I cuticular Ha3-I, Protein Accession O76009, pp. 1-11, last updated Feb. 2009, accessed on Sep. 15, 2014.*
Qingyi Xu, Soybean-based Surfactants and Their Applications, Soybean—Applications and Technology, pp. 341-365, 2011.*
Shakhashiri , www.scifun.org, General Chemistry, Chemical of the Week, Water, pp. 1-7, 2011.*
GenBank Accession No. NP_002271; "keratin, type I cuticular Ha5 [*Homo sapiens*]"; Aug. 4, 2010; whole document.
GenBank Accession No. NP_002274; "keratin, type II cuticular Hb5 [*Homo sapiens*]"; Mar. 28, 2010; whole document.
"Amino Acid-Based Emollient from Ajinomoto"; Ajinomoto; HAPPI, Household & Personal Products Industry; Journal article; Oct. 16, 2001; p. 147; vol. 38, No. 10; World.
Roddick-Lanzilotta, et al; "Anti-Ageing Efficacy in Hair Care Products"; SOFW Journal article; Nov. 2004; pp. 22, 24, 26-28, 30, and 32; vol. 130, No. 11; Germany.
"Cognis Provides Protection"; Soap and Cosmetics; Journal article; Sep. 30, 2001; p. 53; vol. 77, No. 9; World.

(Continued)

*Primary Examiner* — James H Alstrum Acevedo
*Assistant Examiner* — Erinne Dabkowski
(74) *Attorney, Agent, or Firm* — Ohlandt, Greeley, Ruggiero & Perle, L.L.P.

(57) ABSTRACT

A hair treatment composition that contains at least one peptide identical to human hair is provided. The peptide is preferably synthesized from naturally-derived amino acids and can serve as a natural alternative to the commonly used human or animal derived (wool) keratin peptides.

6 Claims, 3 Drawing Sheets

(56) References Cited

OTHER PUBLICATIONS

Niinimeki, et al.; "Contact Urticaria From Protein Hydrolysates in Hair Conditioners"; Allergy; Journal article; Nov. 1998; pp. 1078-1082; vol. 53, No. 11; Denmark.

Han, et al; "Effects of Permanent Waving on Changes of Protein and Physicomorphological Properties in Human Head Hair"; J. Cosmet Sci; Journal article; May/Jun. 2008; pp. 203-215; vol. 59, No. 3; US.

"Formulators Look to Speciality Chemical Companies to Hatch Innovation and Growth Opportunities"; Chemical Market Reporter; Journal article; May 13, 2002; pp. FR3-FR4; USA; World.

"Hair Growth"; Global Cosmetic Industry; Journal article; Jan. 28, 2002; p. 58; vol. 170, No. 1; World.

Onions; "Keratin Peptides Under Evaluation"; Highbeam Business; Journal article; Feb. 1, 1990; whole article; World; http://business.highbeam.com/695/article-1G1-9082421/keratin-peptides-under evaluation.

"L'Oreal Patents Oxidation Composition"; HAPPI, Household & Personal Products Industry; Journal article; Jan. 14, 2008; p. 32; vol. 45, No. 1; US.

"Laboratoires Serobiologiques Launches New Product for Hair Loss"; Parfums, Cosmetiques, Actualites; Journal article; Apr. 12, 2005; p. 81; No. 182; World.

"Natural Ingredients in Personal Care Products"; HAPPI, household & Personal Products Industry; Journal article; Jun. 12, 2001; pp. 81-82, 84, 86, 88-92; vol. 38, No. 6; USA; World.

"New Bioactive Ingredients from Cognis"; Global Cosmetic Industry; Journal article; Sep. 30, 2001; p. 16; vol. 169, No. 3; USA.

"New Hair Care Line From Furterer"; Parfums, Cosmetiques, Actualites; Journal article; Jun. 20, 2005; p. 14; No. 183; World.

"New Seaborne Materials from Presperse"; HAPPI, Household & Personal Products Industry; Journal article; Aug. 10, 1999; p. 150; vol. 36, No. 8; USA.

Rushton; "Nutritional Factors and Hair Loss"; Clinical and Experimental Dermatology; Journal article; 2002; pp. 396-404; vol. 27, No. 5; Oxford, UK.

"Presperse Inc. Launches New Hair Care Products"; Global Cosmetic Industry; Journal article; Aug. 25, 1999; p. 42; vol. 165, No. 2; World.

"R&D In the New Cosmetic Age"; HAPPI, Household & Personal Products Industry; Journal article; Jan. 18, 2001; pp. 56, 58, 60, 62-68; vol. 38, No. 1; World.

"Sabinsa Expands its Actives Portfolio"; Parfums, Cosmetiques Actualites; Journal article; Sep. 30, 2008; p. 125, No. 202; World.

Fox; "Topical Vitamins and Other Topics"; Cosmetics and Toiletries; Journal article; 2004; pp. 30, 32-34, 36; vol. 119, No. 2; US.

"Tri-K Network"; Soap and Cosmetics; Journal article; Jul. 31, 2002; p. 16, vol. 78, No. 5; US.

"Two New Ingredients for Asahi Kasei"; Parfums, Cosmetiques, Actualites; Journal article; Jan. 6, 2006; p. 75; No. 186; World.

"Wacker: Silicones & Cyclodextrin"; SPC, Soap Perfumery and Cosmetics; Aug. 18, 2005; p. 37; vol. 178, No. 8: World.

\* cited by examiner

HAIR TREATMENT COMPOSITION WITH NATURALLY - DERIVED PEPTIDE IDENTICAL TO HUMAN HAIR

FIELD OF INVENTION

Exemplary embodiments of this invention relate to care, strengthening and repair of keratin substrates and in particular of keratin fibers. Exemplary embodiments of the invention relate to compositions comprising at least one natural peptide synthesized from naturally derived amino-acids and of a molecular weight suitable for penetration into the hair shaft. The terminal amino-acids can be selected from those that are substantive to damaged sites on human hair, thus making the peptide able to bind and repair human hair. An additional advantage of exemplary embodiments of the present invention is providing a natural way to repair and reconstruct human hair with human hair identical peptides without using the traditional hydrolyzed human hair or hydrolyzed sheep wool protein.

BACKGROUND OF INVENTION

Keratins are fundamental compounds of the skin, the hair, the eyelashes and the nails. These water-insoluble fibrous proteins contribute towards their form, elasticity and strength. For years now, scientists have been utilizing hydrolyzed proteins to condition and strengthen the hair, and there are both patents and research publications covering the subject. However, hydrolyzed peptides that give the most advantage to hair strength come from human origin or sheep wool. The usage of human and animal products is limited by regulations, ethical and health concerns. Additionally, hydrolyzed wool and human hair proteins can break down into as many as 100-300 fragments. The actual composition, purity and molecular size of these fragments are hard to control and thus the efficacy of hydrolyzed hair is lowered.

Therefore, there is a need to synthesize and make available the specific peptides that are beneficial to hair strength, manageability and overall conditioning and can be substantive to hair using nature-made amino acids.

SUMMARY OF INVENTION

The solid phase peptide synthesis was used to create hair-identical peptides in a precise and controlled manner using natural amino acids as starting materials.

Development started from the review of the published literature on hair structure and selection of the specific Keratin proteins KRT35 and KRT85 that are expressed in the hair-forming matrix of the cortex and cuticles. KRT35 is tied to the basic inner structure of hair and KRT85 is tied to protein cross-linking to enhanced durability, stability, and strength.

Keratin KRT85 is a type II cuticular Hb5. The protein encoded by this gene is a member of the keratin gene family as a type II hair keratin, it is a basic protein which heterodimerizes with type I keratins to form hair and nails.

Keratin KRT35 is type I cuticular Ha5. The protein encoded by this gene is a member of the keratin gene family. This type I hair keratin is an acidic protein which heterodimerizes with type II keratins to form hair and nails.

The next decision was to identify how to lower the molecular weight of these keratins to make them suitable for penetration into the hair shaft. It was decided to terminate the peptides to make them more substantive to hair and the two amino acids that were selected as terminal were: cysteine and arginine.

Cysteine has the largest concentration of amino acid found in hair. Cysteine is an α amino acid with the formula $HO_2CCH(NH_2)CH_2SH$. It is biosynthesized in humans. The side chain on cysteine is thiol, which is non-polar and thus cysteine is usually classified as a hydrophobic amino acid. The thiol is susceptible to oxidization to give the disulfide derivative cystine, which serves an important structural role in hair. It has been proven that cystine participate in disulfide crosslinks and thus have major role in the binding to hair proteins.

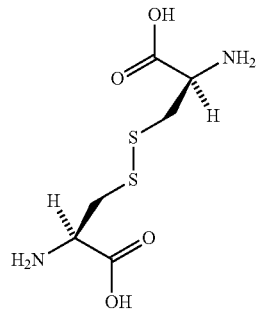 [SMILES: N[C@@H](CSSC[C@H](N)C(=O)O)C(=O)O]

Cystine, as shown above in its neutral form, is derived from two molecules of cysteine connected with a disulfide bond. Cysteine residues play a valuable role by crosslinking proteins which increase the rigidity and strength of hair.

Arginine is also one of the largest components of keratin and has been proven to help with the moisture retention of hair due to its high hydrophilicity. Arginine is a basic amino acid that has a guanidine group that gives it high affinity to hair protein. Arginine is shown below.

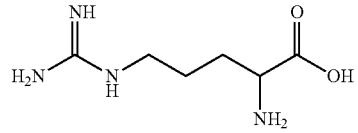

Arginine has been shown to rapidly adsorb to hair on its own, and increase the cosmetic feeling of hair. Therefore, cysteine and arginine where chosen as terminal in the selected sequences.

The following peptides ending in cysteine and arginine were deemed beneficial:

SEQ ID NO: 1 CRSYR
SEQ ID NO: 2 CGVTR
SEQ ID NO: 3 CGSSRSVR
SEQ ID NO: 4 CAPCQPR
SEQ ID NO: 5 CGGLSYSTTPGR
SEQ ID NO: 6 RMIGR
SEQ ID NO: 7 RSGGVC
SEQ ID NO: 8 RAGSCGR
SEQ ID NO: 9 CVPCPGGR
SEQ ID NO: 10 RTNCSPR
SEQ ID NO: 11 CLPAASC
SEQ ID NO: 12 RSFSAC
SEQ ID NO: 13 CLPALC

BRIEF DESCRIPTION OF THE DRAWINGS

Figure 1:
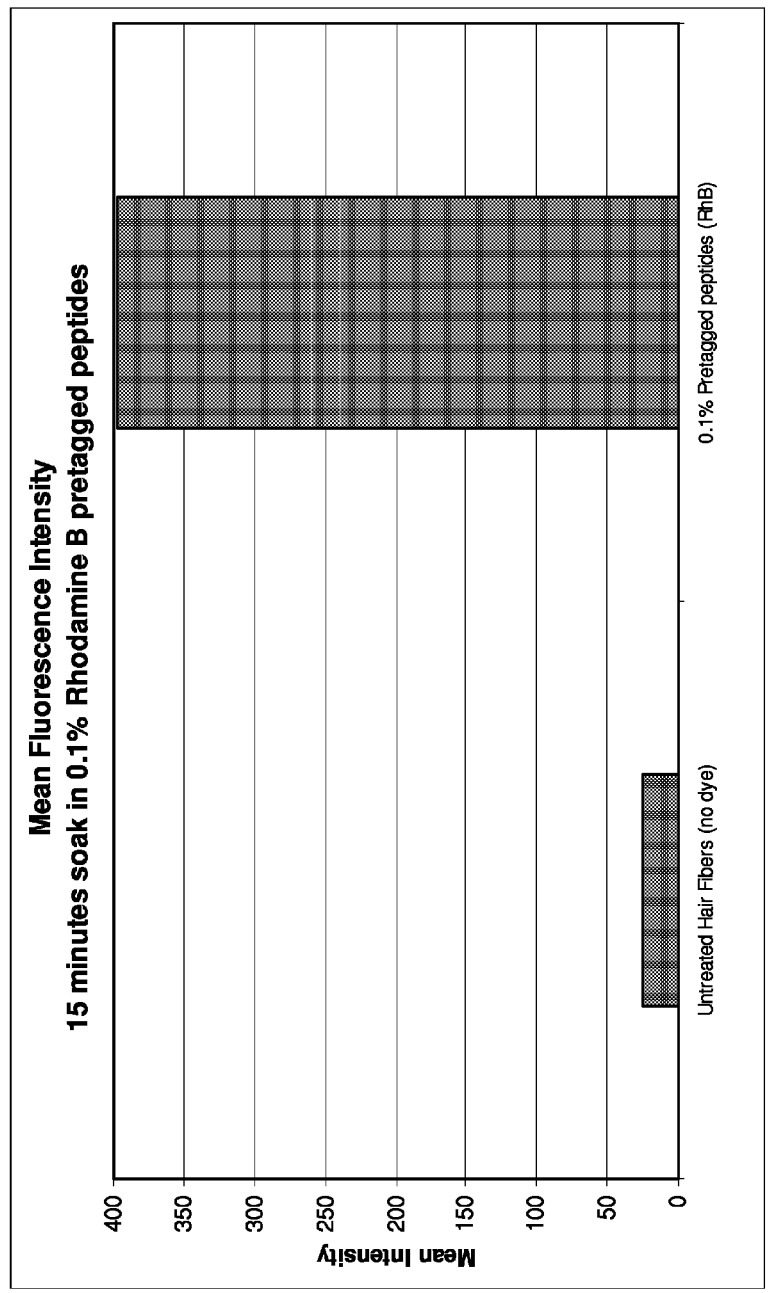
Figure 2:
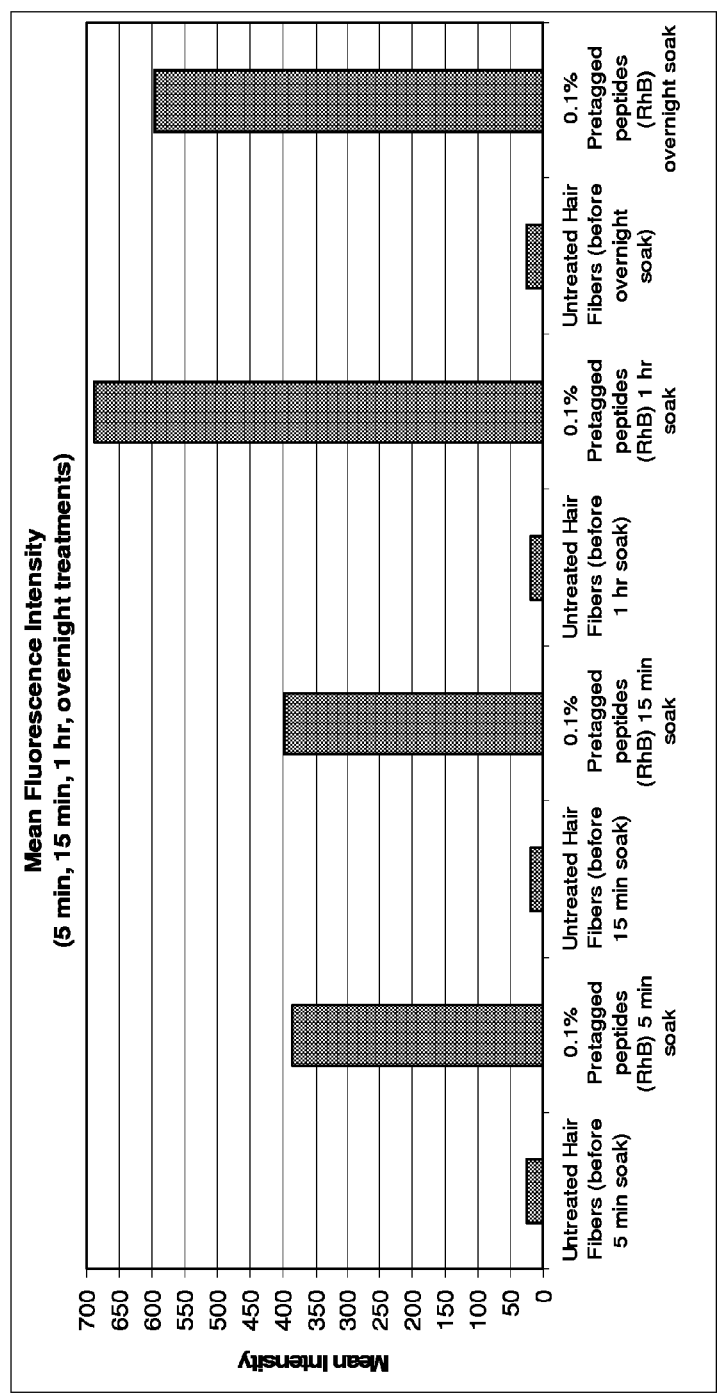
Figure 3:
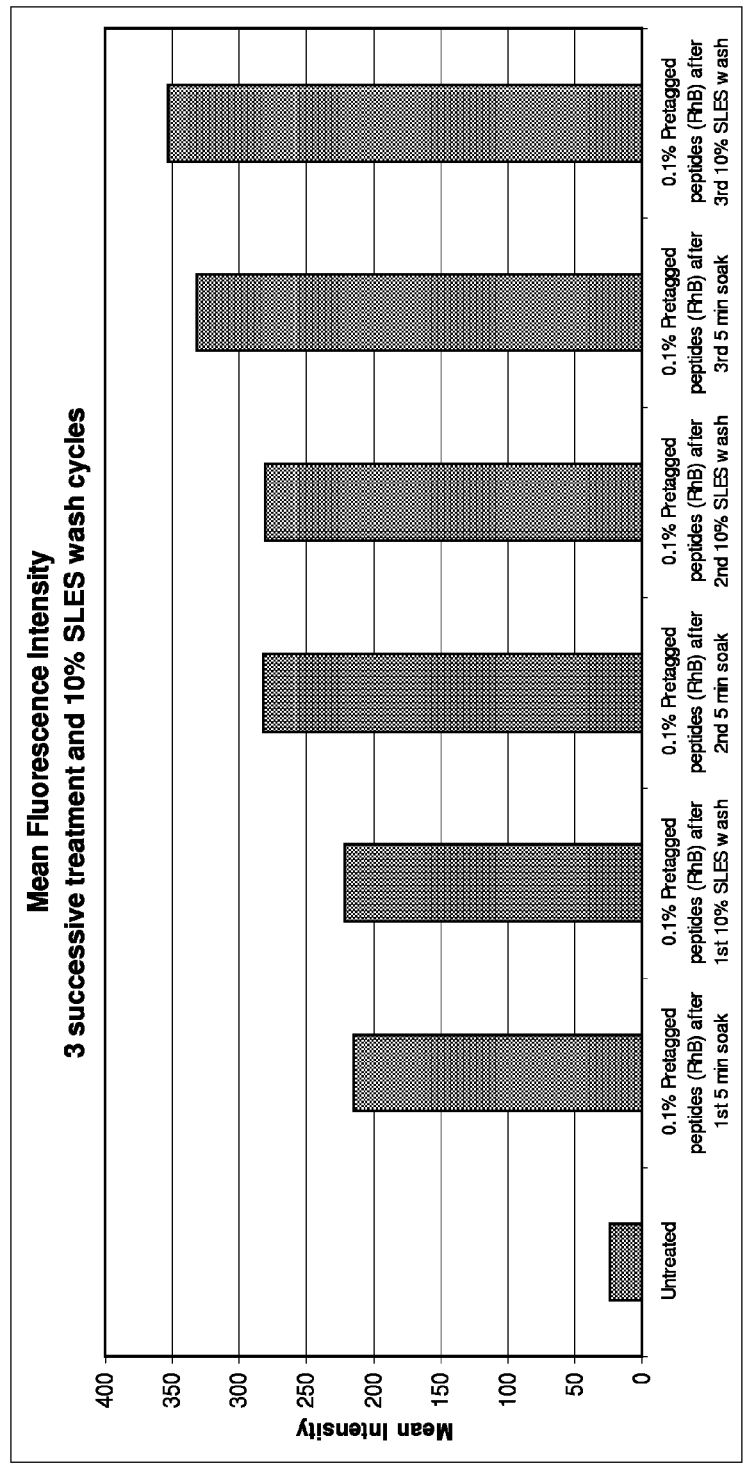

Having thus described the invention in general terms, reference will now be made to the accompanying drawings, where:

FIG. 1 is a chart showing untreated hair fibers compared to hair fibers soaked in Rhodamine B pretagged peptides (0.1% aqueous) for 15 minutes with subsequent water rinse;

FIG. 2 is a chart showing a comparison of mean fluorescence intensity for untreated hair fibers and Rhodamine B pretagged peptides (0.1% aqueous) with 5, 15 and 60 minute and overnight treatments; and FIG. 3 is a chart showing the cumulative effect of a peptide soak and subsequent washing.

DETAILED DESCRIPTION OF THE INVENTION

The invention thus relates to a composition comprising, preferably in a physiologically acceptable medium suitable for topical application to keratin substrates, at least one peptide or peptide fragment prepared from naturally derived amino acids with a molecular weight of 400-2500 Daltons and is capable of penetrating human hair.

The particular peptides that have been found to be useful in the present invention to repair and strengthen damaged human hair are fragments containing at least 3 consecutive amino acids of the selected sequences, preferably of at least 5 amino acids and even more preferentially 5 to 6 consecutive amino acids. The selected amino acids comprise at least one amino acid capable of forming covalent bonds (e.g.: cysteine), hydrogen bonds (e.g.: tyrosine), hydrophobic bonds (e.g.: glycine, valine, leucine) and saline bonds (e.g.: lysine, arginine, histidine, aspartate or glutamate) with other constituent proteins of the hair.

Accordingly, the present invention is directed to a hair dressing treatment comprising a mixture of hair identical peptides synthesized from the following amino-acids: (S) Serine, (Y) Tyrosine, (R) Arginine, (T) Threonine, (G) Glycine, (V) Valine, (F) Phenylalanine, (C) Cysteine, and (L) Leucine, in the selected sequence.

In addition, the composition covered in the present invention may contain hair conditioning ingredients and solvents that can enhance the penetration and deposition of the peptides onto and into the keratin fibers.

EXPERIMENTS

We used human blonde hair purchased from International Hair Importers (Glendale, New York) and bleached it three times with persulfate bleach and 40 volume developer. Substantivity of the peptides to hair was demonstrated via microfluorometry. The peptides were pre-tagged with Sulforhodamine B and applied to hair as a solution soak followed with the subsequent rinsing under running water for 30 seconds. The hair strands were dried and placed under the microscope. The intensity of the fluorometric reading is an indication of the presence and the relative amount of the peptide that is bound to the hair.

Experiment I.

Evaluation of Peptide Deposition on Human Hair Via Microfluorometry Slide Preparation 1. Hair fibers were taken from a 3-times lab bleached tress.
2. The fiber was attached to a square of white tape.
3. Steps 1 and 2 were repeated twice until 3 hair fibers were adhered to the piece of white tape.
4. The hair fibers were then mounted to a glass microscope slide and the ends were secured with adhesive tape.
5. Each hair fiber was labeled consecutively on the white tape.

Microscope Settings:
1. Texas Red Filter was used.
2. 20× Objective was used.
3. Polarized filter was pulled out (no polarization).
4. Camera auto exposure was set to 100 ms.

I. Peptide Deposition
1. The peptide deposition was confirmed by comparing 3-times bleached hair as a control to the hair that was soaked with Rhodamine B pretagged peptide solution for 15 minutes and rinsed with deionized water.

TABLE 1

Untreated hair fibers vs. hair fibers soaked in Rhodamine B pretagged peptides (0.1% aqueous) for 15 minutes

| Sample Name | mean | standard dev |
| --- | --- | --- |
| Untreated Hair Fibers (no dye) | 25.07 | 6.02 |
| 0.1% Rhodamine B pretagged peptides | 396.87 | 80.93 |

FIG. 1 shows untreated hair fiber vs. hair fibers soaked in Rhodamine B pretagged peptides (0.1% aqueous) for 15 minutes with subsequent water rinse.

Conclusions: The hair fibers soaked in Rhodamine B pretagged peptide solution show high fluorescence, therefore confirming the deposition.

Experiment II.

Time-Dependent Penetration of Peptides to Hair

1. The four groups of 3 hair fibers were viewed under the microscope to take the initial readings (Untreated hair) and removed from the slides.
2. Each set of fibers was soaked in peptide solution (peptide was pre-tagged with Rhodamine B) for 5 minutes, 15 minutes, 1 hour and overnight.
3. After soaking, each group was rinsed with deionized (DI) water for 30 seconds and dried.
4. The hair fibers were reattached to a glass microscope slide and the ends were secured with adhesive tape.
5. Readings for mean fluorescence intensity were taken using the Nikon microscope and NIS Elements software.

FIG. 2 shows the mean fluorescence intensity of untreated hair before 5 minute, 15 minute, 1 hour and overnight soak, and the mean fluorescence intensity of hair fibers treated with the peptide solution (peptide pre-tagged with Rhodamine B) with 5 minute, 15 minute, 1 hour and overnight treatments.

Conclusions: There is a definite deposition of peptide on hair even after a 5 minute soak.

The 5 minute and 15 minute soaks in Rhodamine B-peptide solution show similar levels of deposition and are not statistically different from each other. The 1 hour and overnight soaks show higher deposition and are not statistically different from each other either. The 1 hour (and overnight) show higher fluorescent intensity than the 5 and 15 minute soaks, indicating more deposition. It seems that there is enough of an increase in intensity at the 5 minute time point to show that there is uptake and attachment of the peptides.

Experiment III.

Cumulative Effect

1. Untreated readings for mean fluorescence intensity were taken across the hair fibers using the Nikon microscope and NIS Elements software.
2. The hair fibers were detached from the slide and soaked in 0.1% (total active) Rhodamine B pretagged peptide solution for 5 minutes (in a 50 ml beaker with enough solution to cover the fibers) and rinsed in DI water for 30 seconds and dried.
3. The NIS Elements software was used to compute mean fluorescence intensity by taking 6 mean fluorescence intensity readings across each hair fiber (for a total of 18 readings per group) and averaged.
4. Fibers were then washed with 2 drops of 10% sodium lauryl ether sulfate (SLES) (while still on the slide, ends unsecured from the scotch tape), gently lathered for 60 seconds, rinsed for 30 seconds with DI water, and dried.
5. Mean fluorescence intensity readings were taken again.
6. Subsequent soaks, rinses and readings were conducted by repeating steps 2-5 two more times.

FIG. 3 is a chart showing mean fluorescence intensity of three successive treatment and 10% SLES wash cycles. FIG. 3 shows the cumulative effect of the peptide soak and subsequent washing.

Conclusions: The experiment shows that with daily use of peptide solution and subsequent washing of the hair, high level of peptide deposition can be easily achieved and maintained on hair. This effect gives reconstruction, repair, and enhancement in conditioning properties of hair.

The present invention has been described with respect to the preferred embodiment of the invention. It will be clear to those skilled in the art that modifications and/or variations of the disclosed methods and compositions may be made without departing from the scope of the invention set forth herein. The invention is defined by the claims that follow.

What is claimed:

1. A treatment composition comprising:
a mixture of a plurality of synthetic peptides created by solid phase peptide synthesis, wherein the plurality of synthetic peptides comprises a first synthetic peptide and a second synthetic peptide, and wherein each of the first peptide and the second peptide consist of the amino acid sequence selected from the group consisting of CRSYR (SEQ ID NO: 1); CGVTR (SEQ ID NO: 2); CGSSRSVR (SEQ ID NO: 3); CAPCQPR (SEQ ID NO: 4); CGGLSYSTTPGR (SEQ ID NO: 5); RSGGVC (SEQ ID NO: 7); CVPCPGGR (SEQ ID NO: 9); CLPAASC (SEQ D NO: 11); RSFSAC (SEQ ID NO: 12); and CLPALC (SEQ ID NO: 13), and wherein each of the first peptide and the second peptide has a terminal protecting group attached thereto.

2. The treatment composition of claim 1, wherein the plurality of synthetic peptides are each present in molecular weight of 500-700 Daltons to allow easy penetration into the hair.

3. A hair preparation, comprising:
a mixture of a plurality of synthetic peptides created by solid phase peptide synthesis, wherein the plurality of synthetic peptides comprises a first synthetic peptide and a second synthetic peptide, and wherein each of the first peptide and the second peptide consist of the amino acid sequence selected from the group consisting of: CRSYR (SEQ ID NO: 1); CGVTR (SEQ ID NO: 2); CGSSRSVR (SEQ ID NO: 3); CAPCQPR (SEQ ID NO: 4); CGGLSYSTTPGR (SEQ ID NO: 5); RSGGVC (SEQ ID NO: 7); CVPCPGGR (SEQ ID NO: 9); CLPAASC (SEQ D NO: 11); RSFSAC (SEQ ID NO: 12); and CLPALC (SEQ ID NO: 13), and wherein each of the first peptide and the second peptide has a terminal protecting group attached thereto; and cationic conditioners non-ion conditioners, or a combination of the two; and film formers.

4. A hair preparation, comprising:
a mixture of a plurality of synthetic peptides created by solid phase peptide synthesis, wherein the plurality of synthetic peptides comprises a first synthetic peptide and a second synthetic peptide, and wherein each of the first peptide and the second peptide consist of the amino acid sequence selected from the group consisting of: CRSYR (SEQ ID NO: 1); CGVTR (SEQ ID NO: 2); CGSSRSVR (SEQ ID NO: 3); CAPCQPR (SEQ ID NO: 4); CGGLSYSTTPGR (SEQ ID NO: 5); RSGGVC (SEQ ID NO: 7); CVPCPGGR (SEQ ID NO: 9); CLPAASC (SEQ D NO: 11); RSFSAC (SEQ ID NO: 12); and CLPALC (SEQ ID NO: 13), and wherein each of the first peptide and the second peptide has a terminal protecting group attached thereto; and one or more surfactants.

5. A hair coloring composition, comprising:
a mixture of a plurality of synthetic peptides created by solid phase peptide synthesis, wherein the plurality of synthetic peptides comprises a first synthetic peptide and a second synthetic peptide, and wherein each of the first peptide and the second peptide consist of the amino acid sequence selected from the group consisting of: CRSYR (SEQ ID NO: 1); CGVTR (SEQ ID NO: 2); CGSSRSVR (SEQ ID NO: 3); CAPCQPR (SEQ ID NO: 4); CGGLSYSTTPGR (SEQ ID NO: 5); RSGGVC (SEQ ID NO: 7); CVPCPGGR (SEQ ID NO: 9); CLPAASC (SEQ D NO: 11); RSFSAC (SEQ ID NO: 12); and CLPALC (SEQ ID NO: 13), and wherein each of the first peptide and the second peptide has a terminal protecting group attached thereto; and a carrier medium.

6. A treatment composition, comprising:
a mixture of a plurality of synthetic peptides created by solid phase peptide synthesis, wherein the plurality of synthetic peptides comprises a first synthetic peptide, a second synthetic peptide, a third synthetic peptide and a fourth synthetic peptide, and wherein the first synthetic peptide has a sequence consisting of CLPALC (SEQ ID NO: 13), the second synthetic peptide has a sequence consisting of CRSYR (SEQ ID NO: 1), the third synthetic peptide has a sequence consisting of RSFSAC (SEQ ID NO: 12) and the fourth synthetic peptide has a sequence consisting of CGVTR (SEQ ID NO: 2), wherein each of the first peptide, second peptide, third peptide and fourth peptide has a terminal protecting group attached thereto.

* * * * *

SEQUENCE LISTING

```
<160> NUMBER OF SEQ ID NOS: 13

<210> SEQ ID NO 1
<211> LENGTH: 5
<212> TYPE: PRT
<213> ORGANISM: Homo sapien

<400> SEQUENCE: 1

Cys Arg Ser Tyr Arg
1               5

<210> SEQ ID NO 2
<211> LENGTH: 5
<212> TYPE: PRT
<213> ORGANISM: Homo sapien

<400> SEQUENCE: 2

Cys Gly Val Thr Arg
1               5

<210> SEQ ID NO 3
<211> LENGTH: 8
<212> TYPE: PRT
<213> ORGANISM: Homo sapien

<400> SEQUENCE: 3

Cys Gly Ser Ser Arg Ser Val Arg
1               5

<210> SEQ ID NO 4
<211> LENGTH: 7
<212> TYPE: PRT
<213> ORGANISM: Homo sapien

<400> SEQUENCE: 4

Cys Ala Pro Cys Gln Pro Arg
1               5

<210> SEQ ID NO 5
<211> LENGTH: 12
<212> TYPE: PRT
<213> ORGANISM: Homo sapien
```

```
<400> SEQUENCE: 5

Cys Gly Gly Leu Ser Tyr Ser Thr Thr Pro Gly Arg
1               5                   10

<210> SEQ ID NO 6
<211> LENGTH: 5
<212> TYPE: PRT
<213> ORGANISM: Homo sapien

<400> SEQUENCE: 6

Arg Met Ile Gly Arg
1               5

<210> SEQ ID NO 7
<211> LENGTH: 6
<212> TYPE: PRT
<213> ORGANISM: Homo sapien

<400> SEQUENCE: 7

Arg Ser Gly Gly Val Cys
1               5

<210> SEQ ID NO 8
<211> LENGTH: 7
<212> TYPE: PRT
<213> ORGANISM: Homo sapien

<400> SEQUENCE: 8

Arg Ala Gly Ser Cys Gly Arg
1               5

<210> SEQ ID NO 9
<211> LENGTH: 8
<212> TYPE: PRT
<213> ORGANISM: Homo sapien

<400> SEQUENCE: 9

Cys Val Pro Cys Pro Gly Gly Arg
1               5

<210> SEQ ID NO 10
<211> LENGTH: 7
<212> TYPE: PRT
<213> ORGANISM: Homo sapien

<400> SEQUENCE: 10

Arg Thr Asn Cys Ser Pro Arg
1               5

<210> SEQ ID NO 11
<211> LENGTH: 7
<212> TYPE: PRT
<213> ORGANISM: Homo sapien

<400> SEQUENCE: 11

Cys Leu Pro Ala Ala Ser Cys
1               5

<210> SEQ ID NO 12
<211> LENGTH: 6
<212> TYPE: PRT
<213> ORGANISM: Homo sapien

<400> SEQUENCE: 12
```

```
Arg Ser Phe Ser Ala Cys
1               5

<210> SEQ ID NO 13
<211> LENGTH: 6
<212> TYPE: PRT
<213> ORGANISM: Homo sapien

<400> SEQUENCE: 13

Cys Leu Pro Ala Leu Cys
1               5
```